United States Patent [19]

Vcelka et al.

[11] 4,152,378
[45] May 1, 1979

[54] CONTAINER CLOSURE HAVING AUTOMATIC OPENING MEANS

[75] Inventors: John L. Vcelka, Zion, Ill.; David A. Winchell, Twin Lakes, Wis.

[73] Assignee: Baxter Travenol Laboratories, Inc., Deerfield, Ill.

[21] Appl. No.: 777,752

[22] Filed: Mar. 14, 1977

[51] Int. Cl.$^2$ ............................................ A61M 15/00
[52] U.S. Cl. ............................. 261/121 R; 128/187; 215/250; 215/DIG. 3; 220/258; 220/278; 222/541; 261/DIG. 65
[58] Field of Search ................. 220/258, 256, 278; 222/83, 83.5, 85, 86, 541, 507; 261/DIG. 65, 121, 122; 128/187, 194, 185, 186; 215/250, 253, DIG. 3; D24/62

[56] References Cited

U.S. PATENT DOCUMENTS

| | | | |
|---|---|---|---|
| 1,850,911 | 3/1932 | Barlow | 220/258 |
| 3,092,291 | 6/1963 | Franck | 222/83 |
| 3,187,918 | 6/1965 | Moore | 222/83 |
| 3,207,375 | 9/1965 | Bereziat et al. | 222/83 |
| 3,314,429 | 4/1967 | Boehm et al. | 222/83 |
| 3,401,819 | 9/1968 | Salamone | 220/258 |
| 3,802,604 | 4/1974 | Morane et al. | 222/83 |
| 3,844,443 | 10/1974 | Cudzik | 215/337 |
| 4,011,288 | 3/1977 | Assenheimer et al. | 261/DIG. 65 |

FOREIGN PATENT DOCUMENTS 1088508 10/1967 United Kingdom ..................... 215/250

Primary Examiner—Frank W. Lutter
Assistant Examiner—Gregory N. Clements
Attorney, Agent, or Firm—Paul C. Flattery; John P. Kirby, Jr.; Garrettson Ellis

[57] ABSTRACT

A screw top closure for a container opening defining a helically threaded neck, and a rotatable screw top positioned to permit rotation by the screw top between outward and inward positions on the neck. A sealing partition is positioned across the opening of the neck. In accordance with this invention, an aperture is defined in the sealing partition, the aperture being positioned in off-center relation to the rotational axis of the screw top. A sealing cap member is positioned across the aperture, with a rupturable seal, facing the screw top. A projection is defined on the side of the screw top facing the partition, being positioned to be longitudinally spaced from the sealing cap member when the screw top is in the outward position, and to engage the sealing cap member when the screw top is rotationally advanced to its inward position. Accordingly, the seal between the cap member and the partition may be ruptured in aseptic manner by the projection, to open the aperture.

6 Claims, 4 Drawing Figures

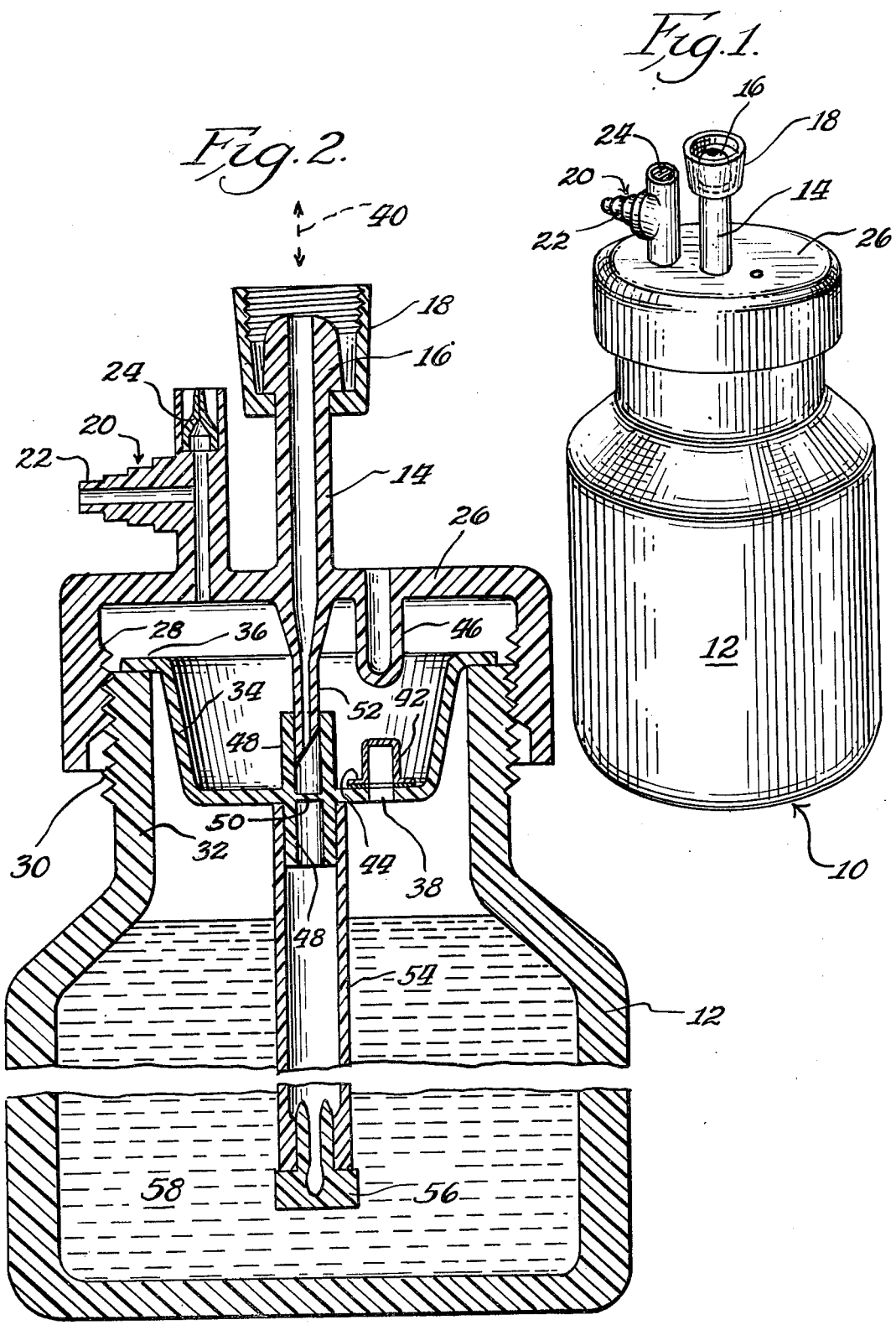

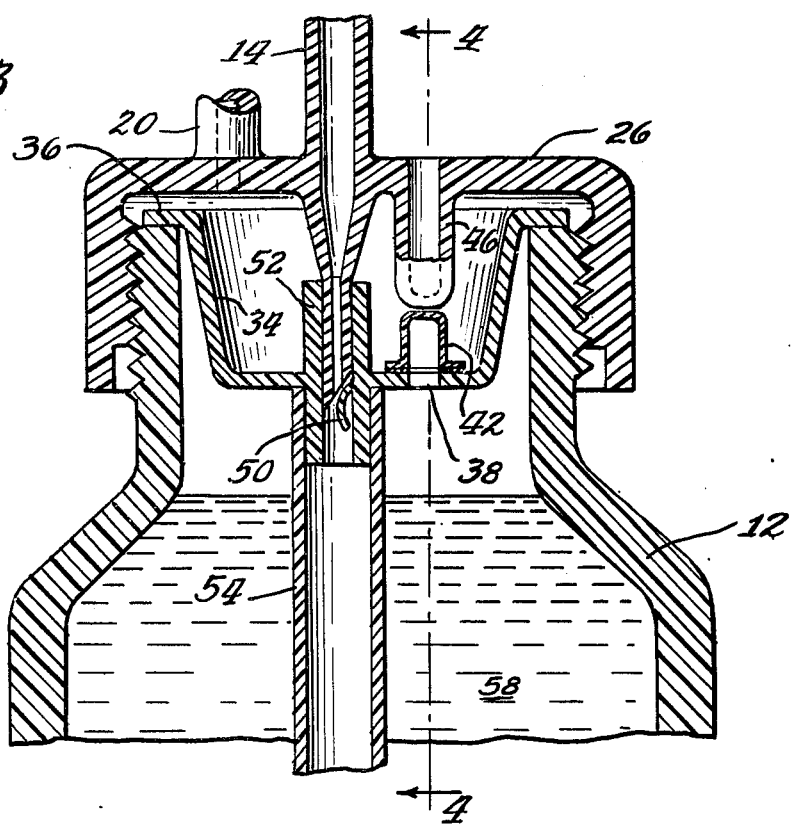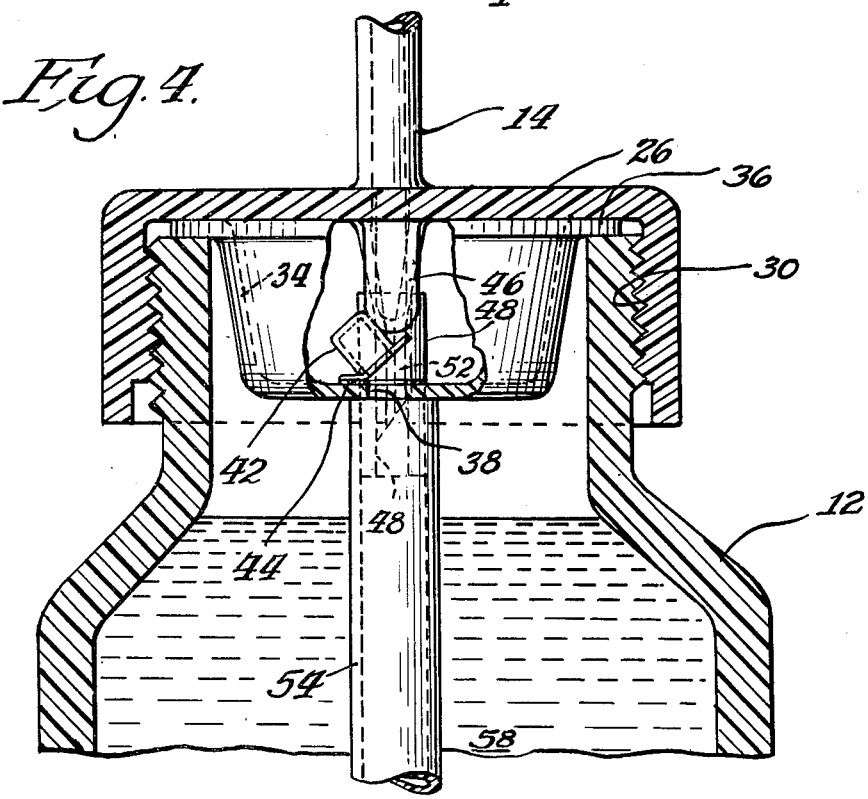

CONTAINER CLOSURE HAVING AUTOMATIC OPENING MEANS

BACKGROUND OF THE INVENTION

This application relates to a closure for gas humidification bottles, or any other desired container in which an inner closure may be aseptically sealed prior to use, and then may be opened by simple rotation of an outer screw closure.

Gas humidifiers are used in conjunction with oxygen gas therapy to patients. Oxygen gas emerging from an oxygen tank has an extremely low humidity. Accordingly, for the comfort and well-being of the patient, the oxygen gas is generally bubbled through water prior to being administered to the patient.

Conventional glass humidifcation canisters must be washed in between uses, and can break. Furthermore, they become a source of bacterial contamination over long use, especially when they have not been adequately washed.

For this reason, disposable plastic humidification containers having aseptic contents have enjoyed considerable commercial success.

One such disposable humidifer is disclosed in Pekkarinen U.S. patent application Ser. No. 558,601, filed Mar. 14, 1975 now issued as U.S. Pat. No. 4,011,288. In this patent application, a screw top closed container is provided with an inner sealing partition, and an outer partition carrying a pair of spikes. A threaded nut member drives the outer partitions toward the inner partition so that the spikes pass through respective tubular sleeves to rupture diaphragms for opening a gas inlet line to the container and a humidified gas outlet path.

The invention of this application provides considerable simplification of the structure necessary to permit opening of an inner partition of a closure by rotation of an outer, threaded member.

The invention of this application eliminates the need for the parallel advancement of a pair of spikes to puncture a pair of membranes as in the patent cited above, and also eliminates the need for a multiple start thread advancement. Also, the parts of this invention do not need to be carefully oriented during assembly, as in the prior art.

Likewise, the device of this invention greatly reduces or eliminates the "spitting" problem of drops of liquid water entering the humidified gas outlet line. Such is, of course, most undesirable when the outlet line leads directly to the breathing apparatus of a patient being administered oxygen.

DESCRIPTION OF THE INVENTION

This invention relates to a screw top closure for a container opening defining a threaded neck including a rotatable screw top, carried by the threaded neck, and having threads mating with the threads of the neck, to permit movement of the screw top by rotation between an outward position and an inward position on the neck. A sealing partition is positioned across the opening of the neck.

In accordance with this invention, an aperture is defined in the partition, positioned in off-center relation to the rotational axis of the screw top. A sealing cap member is positioned across the aperture, being attached with a rupturable seal to the side of the partition facing the screw top.

A projection is defined on the side of the screw top facing the partition, the projection being positioned to be longitudinally spaced from the sealing cap member when the screw top is in its outward position, and to engage the sealing cap member when the screw top is rotationally advanced to the inward position. Accordingly, at the inward position, the projection can be used to push the cap member aside by rotation of the screw top, ripping it loose about its rupturable seal and opening the aperture.

In this manner, the sealed aperture in an inner partition of a closure member can be opened without ever exposing the inner aperture to the exterior. Thus, aseptic conditions can be maintained at the inner closure as the container is opened.

The closure of this invention may also define an upstanding tube passing transversely through the partition positioned across the neck, the tube being generally coaxial with the rotational axis of the screw top. The screw top defines a spike member projecting toward the partition, which is also positioned in generally coaxial relationship with the rotational axis. A diaphragm member is positioned to obstruct the bore of the tube in such a manner that advancement of the screw top by rotation from its outward position toward the inward position on the neck causes the spike to advance through the upstanding tube to rupture the diaphragm.

In this manner, a second, aseptic opening can be provided to the inner partition, one of the openings being useable as an inlet and the other as an outlet for gas, or any other fluid as desired.

In the drawings,

FIG. 1 is a perspective view of a gas humidification device made in accordance with this invention.

FIG. 2 is a vertical sectional view of the device of FIG. 1, with a central portion of the container being omitted.

FIG. 3 is a partial vertical sectional view similar to FIG. 2, showing the device in the process of being opened by rotational advancement of the screw top to an inward position.

FIG. 4 is a partial vertical sectional view taken along line 4—4 of FIG. 3, and shown in a yet further advanced stage of rotational advancement of the screw top, to illustrate the opening of the closure.

Referring to the drawings, humidifier device 10 comprises a container 12, which may desirably be made of plastic and is disposable. The container shown is particularly adapted for hospital use in oxygen administration therapy.

Container 10 defines an oxygen gas inlet port 14 which carries an enlarged head 16, and a loose, threaded nut 18 in conventional manner for attachment to an oxygen outlet at a hospital bedside. Humidified gas outlet 20 comprises a serrated portion 22 for attachment to a nasal cannula, and a pressure relief valve 24, which may be a duck-bill type valve or the like.

Screw top 26 includes inner threads 28 which mate with threads 30 upon the neck 32 of container 12 in the manner of a conventional threaded container lid as shown. Alternatively, more complex threaded structures and arrangements may be utilized as well.

Screw top 26 is shown in FIG. 2 to occupy an outward position on neck 32. By rotation of screw top 26, it is advanced downwardly along the bottle neck to occupy an inward position thereon, as in FIGS. 3 and 4, for opening of the container. A partition 34 is positioned across the opening of neck 32. The periphery 36 of partition 34 may rest upon the outer end of neck 32, being typically attached at the outer end by an adhesive, or by solvent or heat-sealing, or by spin or sonic welding.

Partition 34 defines an aperture 38, which is positioned in off-center relation to the rotational axis 40 of screw top 26. Sealing cap member 42 is positioned across aperture 38. Flange 44 of sealing cap member 42 is attached with a rupturable seal, such as by an appropriate degree of heat sealing, or a solvent seal or sonic seal, to the side of the partition 34 facing screw top 26. Accordingly, sealing cap member 42 closes aperture 38, to prevent fluid transmission through it until it is removed.

As shown, sealing cap member 42 is preferably designed to be of a height which is greater than the diameter of aperture 38, to provide an effective "target" for the projection 46 which is attached to cap 26, and to provide good mechanical advantage for rupturing of the seal member 42.

Projection 46 is shown in FIG. 2 as attached to the underside of cap 26, and is shown to be longitudinally spaced from sealing cap member 42 in the outward position of screw top 26. Specifically, projection 46 is a hollow, integral extension of screw top 26.

When screw top 26 is rotated to advance toward an inward position, projection 46 descends helically toward sealing cap member 42, to engage it as shown in FIG. 3 and then, upon further rotation, as shown in FIG. 4, to rip sealing cap member 42 loose from its rupturable seal to open aperture 38.

Projection 46 and sealing cap member 42 can both be made out of slightly flexible plastic, as the other parts of the container of this invention may also be. However, if desired, projection 46 can be made rigid so that it does not deflect while in the process of ripping sealing cap member loose from its position about aperture 38.

Partition 34 also carries an upstanding tube 48 passing transversely through the partition. Tube 48 is positioned to be coaxial with rotation axis 40 of the screw top, and a diaphragm member 50 is positioned within upstanding tube 48.

Screw top 26 carries a hollow spike member 52 projecting toward partition 34, the spike member being also positioned in a coaxial relationship with axis 40.

Tube 54 may be attached to upstanding tube 48. Tube 54 extends toward the bottom of container 12, and may terminate in a porous sparger member 56, to form small gas bubbles for increased humidification thereof. Sparger member 56 may be made out of porous plastic or ceramic material in a conventional manner.

Accordingly, as screw top 26 is advanced from its outward to its inward position, spike 52 is correspondingly advanced to rupture diaphgram 50, as shown in FIG. 3. Thus, the container of this invention is fully opened by rotation of the screw top 26 to provide a gas inlet path through inlet tube 14, spike 52, past ruptured diaphragm 50, and through sparger tube 54, to bubble through water 58 in container 12.

Thereafter, the humidified gas passes through aperture 38, which is no longer blocked by sealing cap 42, thus passing through partition 34 to the humidified gas outlet 20, for administration to the patient.

The above is for illustrative purposes only, and is not intended to limit the scope of this invention, which is as defined in the claims below.

That which is claimed is:

1. In a screw top closure for a container opening defined by a helically threaded neck, a rotatable screw top, carried by said threaded neck, having threads mating with the threads of said neck, to permit movement of said screw top by rotation between an outward position and an inward position on said neck, and a sealing partition positioned across the opening of said neck, the improvement comprising, in combination:

An aperture defined in said partition, said aperture being positioned in off-center relation to the rotational axis of said screw top; an upstanding sealing cap member with a rupturable seal positioned across said aperture on the side of said partition facing said screw top, and a projection defined on the side of said screw top facing the partition, said projection being positioned to be longitudinally spaced from said sealing cap member when the screw top is in said outward position, and to engage said sealing cap member when the screw top is rotationally advanced more than a complete rotation to said inward position, to rupture the seal between the cap member and the partition, to open said aperture, said partition also defining an upstanding tube passing transversely through said partition, said tube being generally coaxial with the rotational axis of said screw top, said screw top defining a spike member projecting toward said partition, said spike member being also positioned in generally coaxial relationship with said rotational axis, and a diaphragm member positioned to obstruct the bore of said tube, whereby advancement of said screw top by rotation from said outward position to the inward position on said neck causes the spike to rupture said diaphragm.

2. A humidifier for oxygen gas and the like which comprises a liquid-containing reservoir container defining an inlet for oxygen gas and the like, communicating with said upstanding tube, means for conveying said oxygen gas through said upstanding tube in the form of a multitude of bubbles into said liquid, and an outlet, normally spaced from said liquid, for humidified gas, the improvement comprising a screw top closure in accordance with claim 1.

3. The humidifier of claim 2 in which said gas inlet is positioned to lead through said coaxially mounted spike, said coaxial tubular member extending adjacent the bottom of said container to permit the bubbling of gas entering said container through liquid therein.

4. The humidifier of claim 3 in which the gas outlet path leads through said off-center aperture in said partition, and thereafter leads through said humidified gas outlet which is positioned in off-center relation to the rotational axis on said screw top.

5. The humidifier of claim 4 in which the height of said sealing cap member is greater than the width of said aperture in the partition, to facilitate rupturing of said seal by said projection.

6. The screw top closure of claim 1 in which the height of said sealing cap member is greater than the width of said aperture in the partition, to facilitate rupturing of said seal by said projection.

* * * * *